United States Patent

Wade et al.

[11] 4,208,518
[45] Jun. 17, 1980

[54] SUBSTITUTED HYDRAZINO DERIVATIVES OF BENZISOTHIAZOLE-1,1-DIOXIDES

[75] Inventors: Peter C. Wade, Pennington; Thomas P. Kissick, Princeton, both of N.J.

[73] Assignee: E. R. Squibb & Sons, Inc., Princeton, N.J.

[21] Appl. No.: 973,779

[22] Filed: Dec. 27, 1978

Related U.S. Application Data

[62] Division of Ser. No. 875,020, Feb. 3, 1978.

[51] Int. Cl.$^2$ .................. A61K 31/425; C07D 417/12
[52] U.S. Cl. ........................... 544/62; 424/246; 424/247; 424/251; 424/256; 424/270; 544/80; 544/135; 544/357; 544/368; 546/187; 546/198; 546/270; 548/212; 542/419
[58] Field of Search ............... 544/62, 135, 368; 546/256, 270, 187, 198; 260/301, 304 A

[56] References Cited

U.S. PATENT DOCUMENTS

| | | | |
|---|---|---|---|
| 2,751,392 | 6/1956 | Grogan | 260/301 |
| 3,225,056 | 12/1965 | Traverso | 260/301 |
| 3,271,406 | 9/1966 | Traverso | 260/301 |
| 3,457,272 | 7/1969 | Crook | 260/301 |

OTHER PUBLICATIONS

Derwent, Abstract 75731x/41 of Belgian Pat. No. 8402080.
Whitehead et al., J. Med. Chem, 10(5) 840–844, 844–849, 849–852 (1967).

*Primary Examiner*—Donald G. Daus
*Assistant Examiner*—Lisa Jones
*Attorney, Agent, or Firm*—Lawrence S. Levinson

[57] ABSTRACT

Compounds which have the general formula

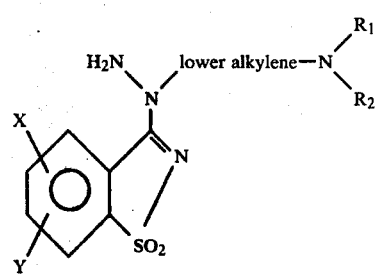

and those which can be obtained from them with a Vilsmeier type reagent and have the formula

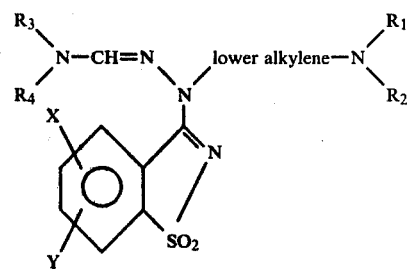

as well as salts thereof, are useful as anti-inflammatory agents.

4 Claims, No Drawings

SUBSTITUTED HYDRAZINO DERIVATIVES OF BENZISOTHIAZOLE-1,1-DIOXIDES

This is a division of application Ser. No. 875,020 filed Feb. 3, 1978.

SUMMARY OF THE INVENTION

This invention relates to new compounds, and acid addition salts thereof, which have the general formula

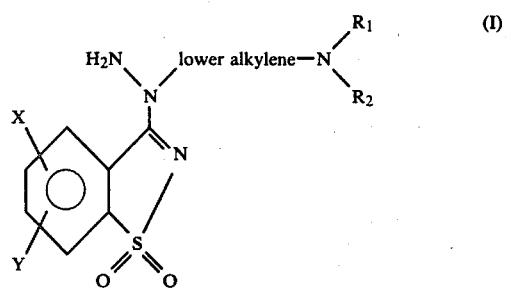

wherein
$R_1$ and $R_2$ each is lower alkyl or together with the nitrogen form a 5- or 6- membered heterocycle,
X is hydrogen, halogen, lower alkyl lower alkoxy or nitro; and
Y is hydrogen, lower alkoxy or halogen.

It also relates to compounds which can be obtained from them with a Vilsmeier type reagent, such as that obtained from phosphorus oxychloride and a formamide having the formula

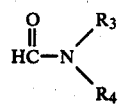

The compounds thus derived have the general formula

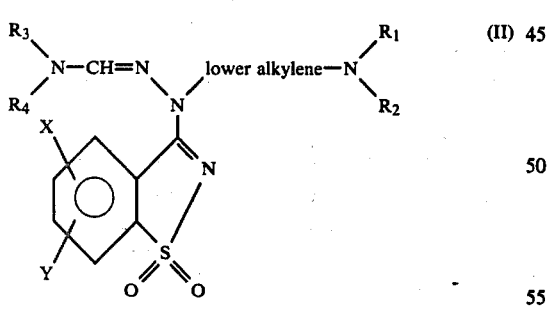

wherein X, Y, $R_1$ and $R_2$ have the same meaning as above, and $R_3$ and $R_4$ have the same meaning as $R_1$ and $R_2$.

DETAILED DESCRIPTION

The lower alkyl groups represented by the symbols are straight or branched chain aliphatic hydrocarbon radicals having up to 7 carbon atoms, for example, methyl, ethyl, propyl, isopropyl, butyl, isobutyl, t-butyl and the like. The $C_1$-$C_4$ and especially the $C_1$-$C_3$ groups are preferred.

The lower alkylene radicals are straight or branched chain groups of the same type having 2 to 7 carbons, with those having up to 4 carbons being preferred.

The lower alkoxy groups are also similar groups having up to 7 carbons like methoxy, ethoxy, propoxy, isopropoxy, butoxy, isobutoxy, t-butoxy, etc. The $C_1$-$C_4$ and especially $C_1$-$C_3$ groups are similarly preferred.

The halogens are the four common halogens, chlorine and bromine being preferred in that order.

When Y is other than hydrogen, X is the same as Y. The amino groups

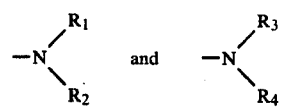

in the compounds of both formula I and formula II, wherein $R_1$, $R_2$, $R_3$ and $R_4$ each represents lower alkyl, include di-lower alkylamino groups like dimethylamino, diethylamino, methylethylamino, dipropylamino, dibutylamino and the like (preferably, but not necessarily, $R_1$ is the same as $R_2$ and $R_3$ is the same as $R_4$ in a given compound). $R_1$ and $R_2$ and/or $R_3$ and $R_4$ can also join with its nitrogen to form one of the 5- or 6-membered heterocyclic radicals pyrrolidino, morpholino, thiamorpholino, piperidino or N-lower alkyl piperazino, e.g., N-methylpiperazino.

The preferred compounds of both formula I and formula II are those wherein X and Y are both hydrogen and $R_1$, $R_2$, $R_3$ and $R_4$ each is lower alkyl, preferably methyl or ethyl, especially the first. The lower alkylene group preferably has 2 to 6 carbons, especially 2 to 4 and most especially 3 carbons.

The products of formula I are produced by reacting a 3-halo-1,2-benzisothiazole, 1,1-dioxide having the formula

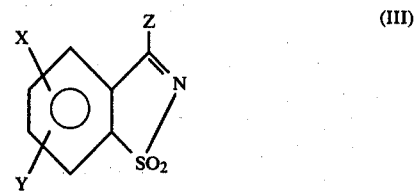

wherein Z is halogen, preferably chlorine or bromine, especially the first,
with an aminoalkylhydrazine having the formula

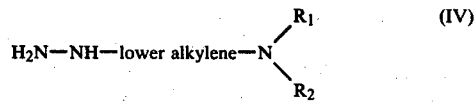

in an inert organic solvent like tetrahydrofuran, dioxane, dimethylformamide, benzene, toluene or the like, at an elevated temperature, preferably about reflux temperature.

The compounds of formula II are then derived from the product of this reaction by treating the compound of formula I with a formamide having the formula

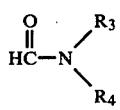

and phosphorus oxychloride, forming a Vilsmeier type reagent in situ. This reaction occurs most conveniently at a temperature in the range of about 10° to 60° C., preferably about room temperature or slightly below.

The starting materials of formula III are produced from saccharin or substituted saccharins which have the formula

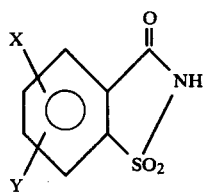

by reaction with thionyl chloride in an inert organic solvent like dioxane in the presence of dimethylformamide catalyst.

The compounds of formula I and formula II form salts which are also part of this invention. The salts include acid-addition salts, particularly the non-toxic, physiologically acceptable members. The bases of formula I and formula II form salts by reaction with an equivalent or more of a variety of inorganic and organic acids providing acid addition salts including, for example, hydrohalides (especially hydrochloride and hydrobromide), sulfate, nitrate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating the salt (which is not necessarily nontoxic) in an appropriate medium in which the salt is insoluble, then after separation of the salt, neutralizing with a base such as barium hydroxide or sodium hydroxide, to obtain the free base. Other salts can then be formed from the free base by reaction with an equivalent or more of acid.

The new compounds of both formula I and formula II have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally or parenterally in dosages of about 5 to 150 mg/kg/day, preferably 10 to 75 mg/kg/day, in single or 2 to 4 divided doses, as indicated by the Mouse Active Arthus or Delayed Hypersensitivity Skin Reaction tests. The active substance may be utilized in compositions such as tablets, capsules, solutions or suspensions containing up to about 500 mg per unit of dosage of a compound or mixture of compounds of formula I or physiologically acceptable acid addition salt thereof. They may be compounded in conventional manner with a physiologically acceptable vehicle or carrier, excipient, binder, preservative, stabilizer, flavor, etc. as called for by accepted pharmaceutical practice.

The following examples are illustrative of the invention. They are representative of and serve as models for the preparation of other members of the class which can be synthesized by replacing each of the reactants with the suitably substituted analog.

EXAMPLE 1

3-[1-[3-(Dimethylamino)propyl]hydrazino]-1,2-benzisothiazole, 1,1-dioxide, hydrochloride (a) 100 g (545 mM) of benzisothiazole 1,1-dioxide, 100 ml. of thionyl chloride, 4 ml. of dimethylformamide (catalyst), and 400 ml. of dioxane are refluxed overnight. Thionyl chloride (50 ml.) and dimethylformamide (1 ml.) are added to the reaction mixture which is again refluxed overnight. The reaction mixture is evaporated to dryness and the residue recrystallized from toluene to obtain 73.4 g. of 3-chloro-1, 2-benzisothiazole-1,1-dioxide, m.p. 140°–145°.

(b) 30.0 g (148 mM) of 3-chloro-1,2-benzisothiazole-1,1-dioxide is dissolved in 200 ml. of dry tetrahydrofuran and then added dropwise over 15 minutes to 17.4 g (148 mM) of dimethylaminopropyl hydrazine in 1.1 of tetrahydrofuran. The resulting mixture is refluxed for 30 minutes. After cooling to room temperature, the yellow solid is filtered off, dissolved in 200 ml. of water, filtered, washed with chloroform, and made basic with 10% sodium hydroxide. The resulting precipitate is filtered off, washed with water, and recrystallized from a mixture of 150 ml. of ethanol and 100 ml. of water to obtain 17.5 g of free base, m.p. 179°–180°.

The free base (4.5 g.) is dissolved in 800 ml. of hot dioxane and the hydrochloride salt is precipitated by the addition of HCl/dioxane. The white solid 3-[1-[3-(dimethylamino)- propyl]hydrazine]-1,2-benzisothiazole, 1,1-dioxide, hydrochloride is collected on a filter, washed with dioxane, and dried at 80° under vacuum; yield 9.7 g, m.p. 265°–267°.

EXAMPLE 2

3-[2-[(Dimethylamino)methylene]-1-[3-dimethylaminopropyl]-hydrazino]-1,2-benzisothiazole, 1,1-dioxide 3.25 ml. (35.5 mM) of phosphorus oxychloride is added to a solution of 10.0 g (35.5 mM) of 3-[1-[3-(dimethyl- amino)propyl]hydrazino]-1,2-benzisothiazole, 1,1-dioxide in 100 ml. of dimethylformamide and stirred in a flask cooled by a water bath. After stirring for 2 hours, the solvent is evaporated and the residue taken up in water which is made basic with 10% sodium hydroxide, then extracted with chloroform. The chloroform extract is washed with water, dried (Na$_2$SO$_4$), and evaporated. The residue, 3-[2-[(dimethylamino)methylene]-1-[3-dimethylamino)propyl]hydrazino]-1,2-benzothiazole, 1,1-dioxide is recrystallized twice from methanol/water; yield 6.4 g, m.p. 119°–121°.

The hydrochloride is formed as in Example 1.

The following additional compounds having the substituents in the table are produced according to the procedures of Example 1 by substituting for the 3-chloro-1,2-benzisothiazole-1,1-dioxide the compound of formula III having the X and Y substituents in the table and substituting for the dimethylaminopropyl hydrazine the hydrazine of formula IV having the substituents in the table:

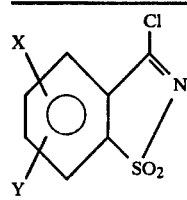

(III)

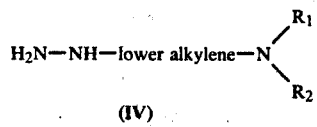

(IV)

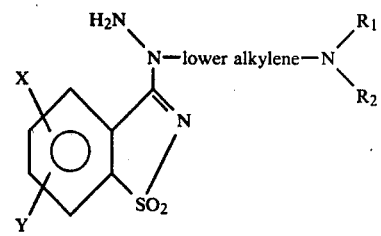

(I)

| Example | X | Y | lower alkylene | $-N\begin{smallmatrix}R_1\\R_2\end{smallmatrix}$ |
|---|---|---|---|---|
| 3 | 6-Cl | H | —(CH₂)₄— | —N(CH₃)₂ |
| 4 | 6-Br | H | —(CH₂)₃— | —N(C₂H₅)₂ |
| 5 | 6-Br | H | —(CH₂)₃— | —N(C₃H₇)₂ |
| 6 | 6-Cl | 7-Cl | —(CH₂)₃— | —N(CH₃)₂ |
| 7 | 8-Cl | 5-Cl | —(CH₂)₂— | —N(CH₃)₂ |
| 8 | H | H | —(CH₂)₆— | —N(pyrrolidinyl) |
| 9 | 6-CH₃ | H | —(CH₂)₂— | —N(morpholinyl) |
| 10 | 6-OCH₃ | 7-OCH₃ | —(CH₂)₂— | —N(4-methylpiperazinyl) |
| 11 | 6-OCH₃ | 7-OCH₃ | —(CH₂)₂— | —N(C₄H₉)₂ |

-continued

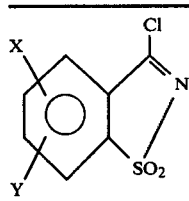

(III)

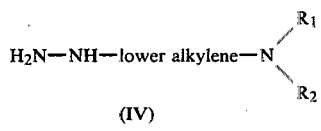

(IV)

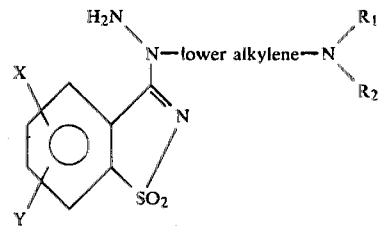

(I)

| Example | X | Y | lower alkylene | $N\begin{smallmatrix}R_1\\R_2\end{smallmatrix}$ |
|---|---|---|---|---|
| 12 | 7-NO$_2$ | H | —(CH$_2$)$_3$— | —N⟨pyrrolidine⟩ |
| 13 | H | H | —(CH$_2$)$_3$— | —N⟨thiomorpholine⟩S |
| 14 | 6-Cl | H | —(CH$_2$)$_4$— | —N⟨piperidine⟩ |
| 15 | H | H | —(CH$_2$)$_5$— | —N⟨piperazine⟩N—C$_2$H$_5$ |
| 16 | 6-OC$_2$H$_5$ | 7-OC$_2$H$_5$ | —(CH$_2$)$_4$— | —N⟨piperazine⟩N—CH$_3$ |
| 17 | 7-OCH$_3$ | 8-OCH$_3$ | —(CH$_2$)$_2$— | —N(CH$_3$)$_2$ |
| 18 | H | H | —(CH$_2$)$_3$— | —N⟨piperidine⟩ |
| 19 | 6-Cl | H | —(CH$_2$)$_2$— | —N⟨thiomorpholine⟩S |

By treating the product of Examples 3 to 19, respectively, according to the procedure of Example 2, substituting for the dimethyl formamide the formamide having the

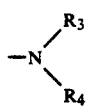

in the table the following products of formula II are obtained:

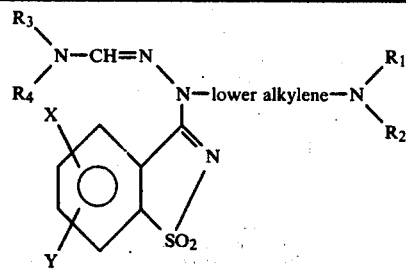

(II)

| Example | X | Y | lower alkylene | $\begin{array}{c}R_1\\-N\\R_2\end{array}$ | $\begin{array}{c}R_3\\-N\\R_4\end{array}$ |
|---|---|---|---|---|---|
| 20 | 6-Cl | H | $-(CH_2)_4-$ | $-N(CH_3)_2$ | $-N(CH_3)_2$ |
| 21 | 6-Br | H | $-(CH_2)_3-$ | $-N(C_2H_5)_2$ | pyrrolidino |
| 22 | 6-Br | H | $-(CH_2)_3-$ | $-N(C_3H_7)_2$ | morpholino |
| 23 | 6-Cl | 7-Cl | $-(CH_2)_3-$ | $-N(CH_3)_2$ | $-N(C_2H_5)_2$ |
| 24 | 8-Cl | 5-Cl | $-(CH_2)_2-$ | $-N(CH_3)_2$ | $-N(C_2H_5)(C_3H_7)$ |
| 25 | H | H | $-(CH_2)_6-$ | pyrrolidino | thiomorpholino |
| 26 | 6-CH$_3$ | H | $-(CH_2)_2-$ | morpholino | morpholino |
| 27 | 6-OCH$_3$ | 7-OCH$_3$ | $-(CH_2)_2-$ | 4-methylpiperazino | $-N(CH_3)_2$ |
| 28 | 6-OCH$_3$ | 7-OCH$_3$ | $-(CH_2)_2-$ | $-N(C_4H_9)_2$ | $-N(CH_3)_2$ |
| 29 | 7-NO$_2$ | H | $-(CH_2)_3-$ | pyrrolidino | piperidino |
| 30 | H | H | $-(CH_2)_3-$ | thiomorpholino | $-N(CH_3)_2$ |

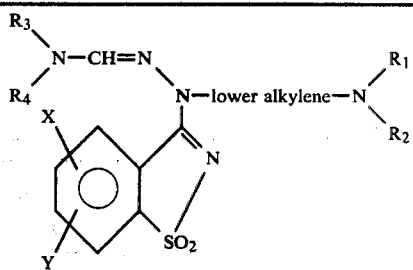

(II)

| Example | X | Y | lower alkylene | $-N\binom{R_1}{R_2}$ | $-N\binom{R_3}{R_4}$ |
|---|---|---|---|---|---|
| 31 | 6-Cl | H | $-(CH_2)_4-$ | piperidino | $-N(CH_3)_2$ |
| 32 | H | H | $-(CH_2)_5-$ | 4-ethylpiperazino | $-N(C_2H_5)_2$ |
| 33 | 6-OC$_2$H$_5$ | 7-OC$_2$H$_5$ | $-(CH_2)_4-$ | 4-methylpiperazino | 4-methylpiperazino |
| 34 | 7-OCH$_3$ | 8-OCH$_3$ | $-(CH_2)_2-$ | $-N(CH_3)_2$ | 4-methylpiperazino |
| 35 | H | H | $-(CH_2)_3-$ | piperidino | $-N(C_2H_5)_2$ |
| 36 | 6-Cl | H | $-(CH_2)_2-$ | thiamorpholino | $-N(CH_3)_2$ |

What is claimed is:

1. A compound of the formula

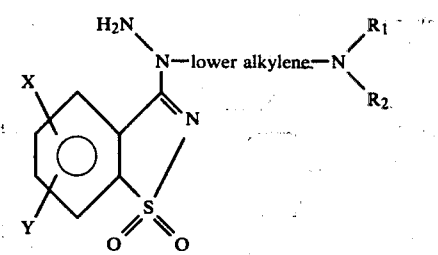

wherein $R_1$ $R_2$ each is lower alkyl or together with the nitrogen form a pyrrolidino, morpholino, thiamorpholino, piperidino or N-lower alkylpiperazino radical; X is hydrogen, halogen, lower alkyl, lower alkoxy or nitro, X being the same as Y when Y is other than hydrogen;

Y is hydrogen, lower alkoxy or halogen;

and acid addition salts thereof.

2. A compound as in claim 1 wherein X and Y each is hydrogen.

3. A compound as in claim 1 wherein $R_1$ and $R_2$ each is lower alkyl, the lower alkylene group has 2 to 6 carbons and X and Y each is hydrogen.

4. A compound as in claim 1 wherein $R_1$ and $R_2$ each is methyl, the lower alkylene group is $(CH_2)_3$ and X and Y each is hydrogen.

* * * * *